(12) United States Patent
Shah et al.

(10) Patent No.: US 9,801,813 B2
(45) Date of Patent: Oct. 31, 2017

(54) PRESERVATIVE-FREE OPHTHALMIC PHARMACEUTICAL FORMULATION

(71) Applicant: Sentiss Pharma Private Limited, New Delhi (IN)

(72) Inventors: Mandar V. Shah, New Delhi (IN); Deepak Bahri, New Dehli (IN); Manish Kumar Singh, New Delhi (IN)

(73) Assignee: Sentiss Pharma Private Limited, New Delhi (IN)

( * ) Notice: Subject to any disclaimer, the term of this patent is extended or adjusted under 35 U.S.C. 154(b) by 0 days.

(21) Appl. No.: 15/028,930

(22) PCT Filed: Oct. 13, 2014

(86) PCT No.: PCT/IB2014/065262
§ 371 (c)(1),
(2) Date: Apr. 12, 2016

(87) PCT Pub. No.: WO2015/056149
PCT Pub. Date: Apr. 23, 2015

(65) Prior Publication Data
US 2016/0235665 A1    Aug. 18, 2016

(30) Foreign Application Priority Data

Oct. 17, 2013   (IN) .......................... 3085/DEL/2013

(51) Int. Cl.
| | |
|---|---|
| *A61K 31/382* | (2006.01) |
| *A61K 31/535* | (2006.01) |
| *A61K 31/5377* | (2006.01) |
| *A61K 9/00* | (2006.01) |
| *A61K 9/08* | (2006.01) |
| *A61K 47/38* | (2006.01) |
| *A61K 47/02* | (2006.01) |
| *A61K 47/12* | (2006.01) |
| *A61K 47/26* | (2006.01) |
| *A61K 45/06* | (2006.01) |

(52) U.S. Cl.
CPC .............. *A61K 9/0048* (2013.01); *A61K 9/08* (2013.01); *A61K 31/382* (2013.01); *A61K 31/535* (2013.01); *A61K 31/5377* (2013.01); *A61K 45/06* (2013.01); *A61K 47/02* (2013.01); *A61K 47/12* (2013.01); *A61K 47/26* (2013.01); *A61K 47/38* (2013.01)

(58) Field of Classification Search
CPC ................ A61K 31/382; A61K 31/535; A61K 31/5377; A61K 9/0048; A61K 9/08; A61K 47/02; A61K 47/12; A61K 47/26; A61K 47/38; A61K 45/06
See application file for complete search history.

(56) References Cited

U.S. PATENT DOCUMENTS 4,438,123 A * 3/1984 Smith .................... A61K 31/28
514/363
6,071,904 A * 6/2000 Ali ....................... A61K 9/0048
514/222.8

FOREIGN PATENT DOCUMENTS

WO     2011/01379 A1     2/2011
WO     WO 2011067791 A2 *  6/2011  ........... A61K 9/0048

OTHER PUBLICATIONS

Rowe, R. et. al., Handbook of Pharmaceutical Excipients, Pharmaceutical Press, 6th ed., pp. 640-642.*
Hercules Incorporated, Aqualon Division, "NATROSOL° Hydroxyethylcellulose: A Nonionic Water-Soluble Polymer," URL=http://brenntagspecialties.com/en/downloads/Products/Multi_Market_Principals/Aqualon/NatrosolHEC_Booklet.pdf, download date Dec. 17, 2013. (24 pages).
The Dow Chemical Company, "CELLOSIZE: Hydroxyethyl Cellulose," URL=http://www.dow.com/assets/attachments/industry/building_construction/Cellosize_brochure.pdf, download date Feb. 3, 2015. (28 pages).

* cited by examiner

*Primary Examiner* — Sarah Pihonak
(74) *Attorney, Agent, or Firm* — Seed IP Law Group LLP (57) ABSTRACT

The present invention relates to a process for manufacturing an ophthalmic formulation of a carbonic anhydrase inhibitor, hydroxyl ethyl cellulose (HEC), and a beta-adrenergic antagonist for use in the treatment of ocular hypertension and glaucoma wherein the ophthalmic pharmaceutical formulation is devoid of benzalkonium chloride or any other preservatives. The present process for manufacturing is simpler, cost effective process to prepare the pharmaceutical ophthalmic formulation in a single tank, without the use of additional tanks that can be sterile filtered.

18 Claims, 2 Drawing Sheets

PRESERVATIVE-FREE OPHTHALMIC PHARMACEUTICAL FORMULATION

FIELD OF THE INVENTION

The present invention relates to the process of manufacturing pharmaceutical formulation for topical administration comprising a therapeutically effective amount of carbonic anhydrase inhibitor or ophthalmologically acceptable salts thereof and a therapeutically effective amount of hydroxyl ethyl cellulose (HEC), to be used for the treatment of ocular hypertension and glaucoma wherein the said ophthalmic pharmaceutical formulation is devoid of benzalkonium chloride or any other preservatives.

BACKGROUND OF THE INVENTION

Glaucoma is a degenerative disease of the eye wherein the intraocular pressure is too high to permit normal eye function. As a result, damage may occur to the optic nerve head and result in irreversible loss of visual function. If untreated, glaucoma may eventually lead to blindness.

Ocular hypertension, i.e., the condition of elevated intraocular pressure without optic nerve head damage or characteristic glaucomatous visual field defects, is now believed by the majority of ophthalmologists to represent merely the earliest phase in the onset of glaucoma.

Management of open angle glaucoma and ocular hypertension require long term treatment with eye drops containing preservatives. Use of preservative containing eye drops has been implicated in the development or worsening of ocular surface disease.

Symptoms and signs of ocular surface disease such as ocular surface breakdown, irritation, burning, foreign body sensation, dryness, inadequate quantity of tears, etc. are prevalent in a large proportion of patients with open angle glaucoma and ocular hypertension.

It is well known in the prior art that small organic compounds, such as benzalkonium chloride (BAC), chlorhexidine, thimerosal have excellent antimicrobial activity; however, it is now known that these small organic antimicrobials are often toxic to the sensitive tissues of the eye and can accumulate in cornea, contact lenses, particularly soft, hydrophilic contact lenses. Medications with BAC may cause disruption of the corneal surface with lower concentrations of BAC.

Gasset and Grant et al. showed that BAC accumulates in ocular tissue and remains there for long periods, adversely affecting both the corneal surface and the conjunctiva. Therefore, cessation of the medications may not immediately improve the condition and function of the ocular surface. These findings also suggest that corneal cell necrosis may occur in some patients who are taking multiple BAC-preserved ocular medications over long periods of time, even when the amount of BAC in any one medication is below the threshold concentration at which necrosis occurs.

Compared to eye drops preserved with benzalkonium chloride, preservative-free eye drops induce significantly fewer ocular symptoms and signs of irritation in patients, such as pain or discomfort, foreign body sensation, stinging or burning, and dry eye sensation.

Patients experiencing hypersensitivity reactions with benzalkonium chloride or any other kind of preservatives cannot use a commercial dorzolamide and timolol product containing benzalkonium chloride which is preserved even with 0.0075% w/v or even with as 0.005% w/v benzalkonium chloride.

Representative CAIs are disclosed in: U.S. Pat. No. 4,797,413 (Baldwin, et al.), U.S. Pat. No. 4,847,289 (Baldwin, et al.), and U.S. Pat. No. 4,731,368 (Hoffman, Jr., et al.); U.S. Pat. No. 5,153,192 (Dean, et al.), U.S. Pat. No. 5,240,923 (Dean, et al.), and U.S. Pat. No. 5,378,703 (Dean, et al.); PCT/US91/02262 (filed 9 Apr. 1990); and EP 452 151 (published 16 Oct. 1991). The entire contents of each of the above-mentioned patents and patent applications are incorporated herein by reference.

Hence, there is an unmet medical need to prepare a preservative-free ophthalmic pharmaceutical formulation wherein the preservative-free formulation induces significantly fewer ocular symptoms and signs of irritation in patients, such as pain or discomfort, foreign body sensation, stinging or burning, and dry eye sensation.

The present invention relates to the process of manufacturing pharmaceutical formulation for topical administration comprising a therapeutically effective amount of carbonic anhydrase inhibitor or ophthalmologically acceptable salts thereof and a therapeutically effective amount of hydroxyl ethyl cellulose (HEC) in combination with timolol, to be used for the treatment of ocular hypertension and glaucoma.

In the prior art various techniques were used in the pharmaceutical industry to make the high viscosity products sterile. Steam sterilization or autoclaving of ophthalmic dosage forms is common practice in pharmaceutical industry. It involves heating the ophthalmic solution or suspension, to be sterilized, placed in suitable container, at 121° C. for about 15-20 minutes. However, in many cases it is not advisable due to heat sensitivity of the drug or excipients, incompatibility of excipients with drug at higher temperature and cost involved.

In spite of that in the present formulation the inventors are using thickening agents such as HEC which is capable of building the viscosity of the solution in combination with active ingredients.

Major problems related to the ophthalmic formulations comprising HEC are that commercially HEC is available in two molecular weight range i.e. 1.0 and 1.3 million Dalton having an approximate diameter of around 0.1 and 0.13 microns respectively (assuming spherical shape) as shown in Table 1. Since the diameter of HEC is very close to the pore size of the filter, it is not possible to filter HEC through sterilizing filter, having the pore size of 0.22 microns.

TABLE 1

Relationship between molecular weight and approximate molecular diameter.

| Molecular weight (Dalton) | Diameter (Micron) |
|---|---|
| 1,000,000 | 0.1 |
| 1,300,000 | 0.13 |

In-situ sterilization of HEC solution is possible. However, in-situ sterilization of HEC results in significant loss of viscosity as shown in Table 2. Further, even after loss of viscosity of HEC, it is not possible to pass the HEC solution through sterilization grade of filters.

TABLE 2

Effect of temperature at 121° C. for various times on viscosity of HEC.

| Condition | Low Viscosity (HEC 250 HX - 1.0%) | High Viscosity (HEC 250 HHX - 0.9%) |
|---|---|---|
| Initial | 116 cps | 247.5 cps |
| After 121° C./1 hrs | 93.3 cps | 255.3 cps |
| After 121° C./2 hrs | 57.3 cps | 178.6 cps |
| After 121° C./3 hrs | 55.7 cps | 164 cps |
| After 121° C./4 hrs | 33.7 cps | 111 cps |

Figure 1:
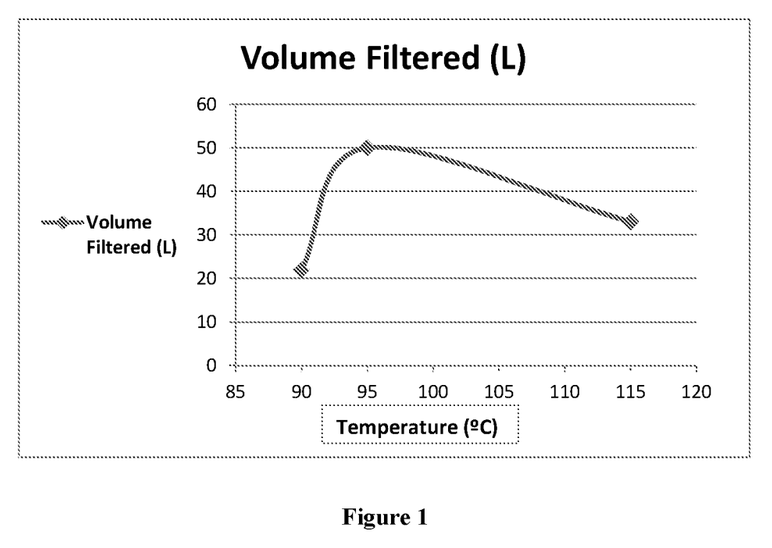
FIG. 1: Showing the volume of solution filtered when exposed to various temperatures for various lengths of time to achieve the viscosity of 100±10 cps.

The inventors of the present invention surprisingly have discovered a narrow window of heating HEC solution such that minimal loss of viscosity occurs and it is possible to filter the HEC solution through aseptic filtration technique. It involves slow heating the ophthalmic solution or suspension, within a narrow window temperature range between from about 94° C. to from about 97° C. through a sterilization filter of pore size of 0.22 microns while still achieving the viscosity of 100±10 cps as shown in FIG. 1. While working on the development of the present ophthalmic solution dosage form, present inventors have embarked upon a simple technique, which eliminates the steam sterilization and/or autoclaving.

The present inventors have now developed simpler and cost effective process(es) to prepare pharmaceutical ophthalmic formulations in a single tank, without the use of additional tanks that can be sterile filtered.

OBJECTS OF THE PRESENT INVENTION

The main object of the present invention is to provide a process of manufacturing ophthalmic pharmaceutical formulation comprising a therapeutically effective amount of carbonic anhydrase inhibitor or ophthalmologically acceptable salts thereof and a therapeutically effective amount of hydroxyl ethyl cellulose (HEC).

Yet another object of the present invention is to provide a process for manufacturing ophthalmic pharmaceutical formulation in combination with beta-adrenergic antagonist or, an ophthamically acceptable salt thereof.

Yet another object of the present invention is to provide a process which is simpler and cost effective.

Yet another object of the present invention is to provide a process for manufacturing ophthalmic pharmaceutical formulation in a single tank and without the use of additional tanks that can be sterile filtered.

Yet another object of the present invention is to provide the ophthalmic pharmaceutical formulation which is devoid of benzalkonium chloride or any other preservative.

SUMMARY OF THE PRESENT INVENTION

The present invention relates to the process of manufacturing pharmaceutical formulation for topical administration comprising a therapeutically effective amount of carbonic anhydrase inhibitor or ophthalmologically acceptable salts thereof and a therapeutically effective amount of hydroxyl ethyl cellulose (HEC), to be used for the treatment of ocular hypertension and glaucoma.

In another embodiment, the present invention relates to the process of manufacturing ophthalmic pharmaceutical formulation for topical administration comprising a therapeutically effective amount of carbonic anhydrase inhibitor or ophthalmologically acceptable salts thereof and a therapeutically effective amount of hydroxyl ethyl cellulose (HEC) in combination with a beta-adrenergic antagonist selected from but not limited to timolol, betaxolol, bufenolol, carteolol, levobunolol and metipranolol or an ophthalmologically acceptable salt thereof.

In yet another embodiment, the said ophthalmic pharmaceutical formulation is devoid of benzalkonium chloride or any other preservatives which will be superior from a safety & tolerability standpoint while maintaining and/or improving its efficacy to lower increased intraocular pressure in ocular hypertension and glaucoma.

In a preferred embodiment, the present invention relates to the process of manufacturing ophthalmic pharmaceutical formulation for topical administration comprising dorzolamide and hydroxyl ethyl cellulose (HEC) in combination with timolol.

In an another preferred embodiment of the invention, at least one surfactant, at least one isotonicity agent, at least one viscosity enhancing agent, at least one antioxidant and at least one pH adjusting agent are added to the above ophthalmic pharmaceutical formulation.

In further embodiment, the present inventors have embarked upon a simple technique, which eliminates the steam sterilization or autoclaving with minimal loss of viscosity and better stability, as shown by reduced formation of impurity B of active ingredient Dorzolamide.

In yet a further embodiment, the present inventors have developed simpler and cost effective process(es) to prepare pharmaceutical ophthalmic formulations in a single tank, without the use of additional tanks that can be sterile filtered.

DETAILED DESCRIPTION OF THE INVENTION

As used herein, the term "BAC" wherever appears is an abbreviation for "benzalkonium chloride".

As used herein, the term "CAIs" wherever appears is an abbreviation for "carbonic anhydrase inhibitors".

As used herein, the term "HEC" wherever appears is an abbreviation for "hydroxylethyl cellulose".

As used herein, the term "cps" wherever appears is an abbreviation for "Centipoise".

As used herein, the term "Control product" wherever appears is the U.S. FDA approved product "COSOPT-PF".

As used herein, the term "NMT" wherever appears is an abbreviation for "not more than".

As used herein, the term "BDL" wherever appears is an abbreviation for "below detection limit".

As used herein, the term "ND" wherever appears is an abbreviation for "None detected".

As used herein, the term "PP" wherever appears is an abbreviation for "polypropylene".

As used herein, the term "PES" wherever appears is an abbreviation for "polyether sulfone". As used herein, wherever the drug comprises dorzolamide, the impurities preferably measured include Impurity D {(4S,6S)-4-Amino-6-methyl-5,6-dihydro-4H-thieno[2,3-b]thiopyran-2- sulfonamide7,7-dioxide hydrochloride} & B {(4RS,6SR)-4-(Ethylamino)-6-methyl-5,6-dihydro-4H-thieno[2,3-b]thiopyran-2-sulfonamide 7,7-dioxide hydrochloride}.

As used herein, wherever the drug comprises timolol, the impurities preferably measured include Impurity G {4-Morpholino-1,2,5-thiadiazol-3-ol 1-oxide}; B {3-(tert-Butylamino)-2-(4-morpholino-1,2,5-thiadiazol-3-yloxy)propan-1-ol} and D {4-Morpholino-1,2,5-thiadiazol-3-ol}.

In an embodiment, the present invention relates to the process of manufacturing ophthalmic pharmaceutical formulation for topical administration comprising a therapeutically effective amount of a carbonic anhydrase inhibitor or ophthalmologically acceptable salts thereof and a therapeutically effective amount of hydroxyl ethyl cellulose (HEC) in combination with a beta-adrenergic antagonist selected from but not limited to timolol, betaxolol, bufenolol, carteolol, levobunolol and metipranolol or an ophthalmologically acceptable salt thereof.

In another embodiment, the said ophthalmic pharmaceutical formulation is devoid of benzalkonium chloride or any other preservatives which will be superior from a safety & tolerability standpoint while maintaining and/or improving its efficacy to lower increased intraocular pressure in ocular hypertension and glaucoma.

In a preferred embodiment, the present invention relates the process of manufacturing ophthalmic pharmaceutical formulation for topical administration comprising dorzolamide and hydroxyl ethyl cellulose (HEC) in combination with timolol and/or ophthalmologically acceptable carriers.

Figure 2:
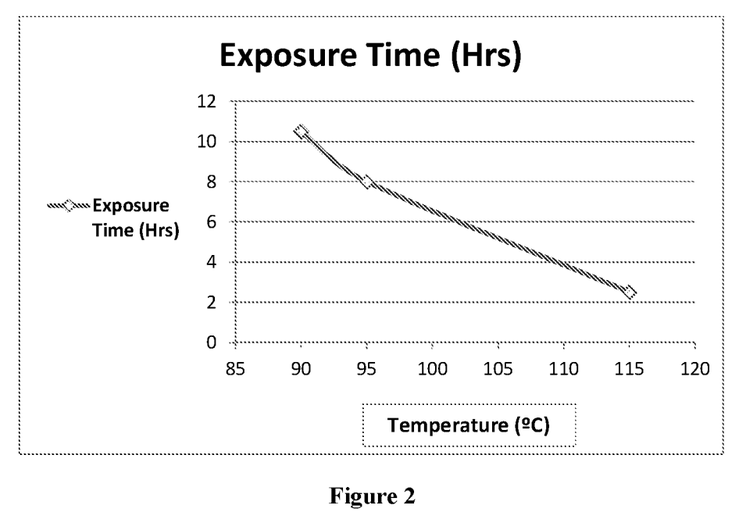
FIG. 2: Showing the exposure time in hours to achieve the viscosity of 100±10 cps at various temperatures.
Figure 3:
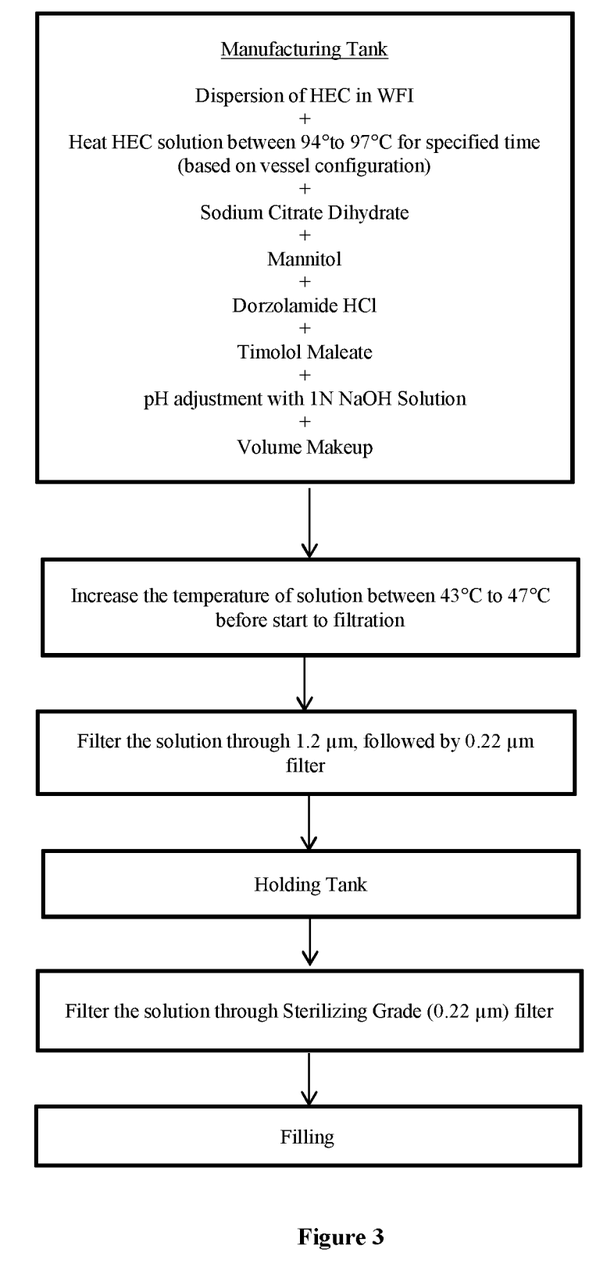
FIG. 3: Showing the manufacturing process comprising a combination of dorzolamide and timolol.

In a further embodiment, the inventors of the present invention surprisingly have discovered a narrow window of heating HEC solution such that minimal loss of viscosity occurs and it is possible to filter the HEC solution through aseptic filtration technique. It involves slow heating the ophthalmic solution or suspension, within a narrow window temperature range between from about 94° C. to from about 97° C. for sufficient time to produce a mixture with a viscosity of about 100±10 cps as shown in FIG. 1. The mixture can be sterilized by passing it through a sterilization filter, where the pore size of the filter may be about 0.2 microns. In yet other embodiment, this narrow window temperature range between from about 94° C. to from about 97° C. is achieved by performing various in-house experiments when exposed to various temperatures for various lengths of time to achieve the viscosity of 100±10 cps and volume of solution filtered through sterilization filter of pore size of 0.22 microns as shown in FIGS. 1 and 2.

In an embodiment, the present inventors have developed simpler and cost effective process(s) to prepare pharmaceutical ophthalmic formulations in a single tank, without the use of additional tanks that can be sterile filtered.

In other embodiment, the present ophthalmic solutions containing thickening agents such as one or more cellulose polymers are manufactured by aseptic techniques. In this technique the active ingredients, the polymer solution of the HEC and other ingredients are dissolved in water for injection in a single tank and filter sterilized through 0.22 micron filter. Then the whole solution is filled aseptically into the containers.

In another embodiment, since aseptic filing of the dorzolamide and HEC in combination with timolol solution takes place at a lower temperature (95° C.) there is no heat incompatibility issue.

In one embodiment of the present invention, there is an aseptically filtered ophthalmic solution comprising dorzolamide or salt thereof, one or more thickening agent in combination with timolol optionally with ophthalmically acceptable carriers.

In other embodiment, there is provided a process for preparation of ophthalmic solution comprising dorzolamide or salt thereof, HEC in combination with timolol wherein the said process comprises of aseptic filtration and filing in to the desired container, a solution containing dorzolamide or salt thereof, HEC in combination with timolol optionally with ophthalmically acceptable carriers.

In another embodiment, the present invention relates to the process of manufacturing pharmaceutical formulation for topical administration comprising a therapeutically effective amount of dorzolamide or ophthalmologically acceptable salts thereof and a therapeutically effective amount of hydroxyl ethyl cellulose (HEC) in combination with timolol, to be used for the treatment of ocular hypertension and glaucoma.

In yet another embodiment, the present invention relates to the process of manufacturing pharmaceutical formulation to be used for the treatment of ocular hypertension and glaucoma wherein the said ophthalmic pharmaceutical formulation is devoid of benzalkonium chloride or any other preservatives.

In further embodiment, the said ophthalmic pharmaceutical formulation will be superior from a safety & tolerability standpoint while maintaining and/or improving its efficacy to lower increased intraocular pressure in ocular hypertension and glaucoma.

In other further embodiment, the invention relates to the use of dorzolamide and hydroxyl ethyl cellulose (HEC) in combination with timolol sterilized by aseptic filtration for the manufacture of ophthalmic compositions.

In yet further embodiment, the present invention relates to methods of manufacturing pharmaceutical formulation for topical administration comprising a therapeutically effective amount of carbonic anhydrase inhibitor or ophthalmologically acceptable salts thereof and a therapeutically effective amount of hydroxyl ethyl cellulose (HEC), to be used for the treatment of ocular hypertension and glaucoma wherein the said ophthalmic pharmaceutical formulation is devoid of benzalkonium chloride or any other preservatives.

The present invention is directed to methods for treating patients with glaucoma or ocular hypertension wherein their IOP can only be controlled by the use of two IOP lowering drugs, namely, carbonic anhydrase inhibitors and a beta-adrenergic antagonist. These drugs may be dosed simultaneously and be formulated in a single composition to provide for convenience and patient compliance.

More particularly, the present invention is available for use by patients hypersensitive to benzalkonium chloride and/or any other preservative.

The present invention is directed to formulations of dorzoalmide and timolol without benzalkonium chloride as a preservative and may be marketed in unit dose form.

Other side effects which may be avoided with this preservative-free formulations of the present invention include, blepharitis, corneal erosion, depression, epiphora, eye discharge, eye dryness, eye irritation, eye pain, eyelid edema, eyelid erythema, eyelid pruritus, foreign body sensation, headache, hypertension, oral dryness, somnolence, superficial punctate keratitis, and visual disturbance.

The CATs which are useful in the formulations and methods of the present invention include all thiophene sulfonamides and thienothiazines such as brinzolamide, acetazolamide and dorzolamide which lower and control IOP by inhibiting carbonic anhydrase when administered topically.

Preferred CATs of the present invention has been described chemically as: (4S-trans)-4-(ethylamino)-5,6-dihydro-6-methyl-4H-thieno[2,3-b]thiopyran-2-sulfonamide 7,7-dioxide monohydrochloride (dorzolamide). The carbonic anhydrase inhibitors of this invention accordingly may be used as diastereomeric mixtures or single enantiomers or as racemic mixtures and is optically active.

The beta-adrenergic antagonist of the present formulation is selected from timolol, betaxolol, bufenolol, carteolol, levobunolol and metipranolol or an ophthalmologically acceptable salt thereof.

Most of the beta-adrenergic antagonists and carbonic anhydrase inhibitors recited above have at least one asymmetric carbon atom and accordingly may exist as diastereomers or (+)- or (−)-enantiomers. This invention contemplates the use of any of the diastereomers or enantiomers or mixtures thereof including racemic forms.

The preferred beta-adrenergic antagonist for use in the formulation of present invention is timolol as its maleate salt and is described chemically as: (−)-1-(tert-butylamino)-3-[(4-morpholino-1,2,5-thiadiazol-3-yl)oxy]-2-propanol maleate (1:1) (salt).

In one of the embodiments, the present formulations of this invention comprise from about 0.05 to 5% (w/w) of carbonic anhydrase inhibitor, usually about 0.5 to 3% (w/w) and from about 0.01 to 1% (w/w) of beta-adrenergic antagonist, preferably about 0.1 to 0.5% (w/w).

In another embodiment, the present formulations of this invention may be administered topically in the form of solutions, gels, ointments, suspensions or solid inserts, formulated so that a unit dosage comprises a therapeutically effective amount of each active component thereof.

Further in another embodiment, the ophthalmic formulation may be prepared by using ophthalmically acceptable carrier components. Ophthalmically acceptable carriers of the present invention includes, without limited to, thickening agent, buffering agents, emulsifying agents, chelating agents, wetting agents, tonicity adjusting agents, permeation enhancers, surfactants, pH adjusting agents and the like.

Further in yet another embodiment, typical ophthalmologically acceptable carriers for the present formulations are, for example, water, mixtures of water and water-miscible solvents such as lower alkanols or aralkanols, vegetable oils, polyalkylene glycols, petroleum based jelly, ethyl cellulose, ethyl oleate, carboxymethylcellulose, polyvinylpyrrolidone, isopropyl myristate and other conventionally employed acceptable carriers.

Furthermore in one of the embodiments, buffering agents used in the present invention includes but are not limited to acetate buffers, citrate buffers, phosphate buffers, sodium dihydrogen phosphate dihydrate, dibasic sodium phosphate heptahydrate, monobasic sodium phosphate, citric acid, citric acid monohydrate or ε-aminocaproic acid and the like.

Furthermore in another embodiments, the present invention may include chelating agents but not limited to edetate salts like disodium edetate or ethylenediamine tetraacetic acid ("EDTA"), edetate calcium disodium, edetate sodium, edetate trisodium, and edetate dipotassium, diammonium EDTA, dipotassium EDTA, calcium disodium EDTA, hydroxyethylethylenediaminetriacetic acid ("HEDTA"), ethylenediaminetetraacetic acid, mono(triethanolamine) salt ("TEA-EDTA"), tetrasodium EDTA, tripotassium EDTA, trisodium phosphate, diammonium citrate, galactaric acid, galacturonic acid, gluconic acid, glucuronic acid, cyclodextrin, potassium citrate, the potassium salt of ethylenediamine-tetra (methylene phosphonic acid) ("EDTMP"), sodium citrate, sodium EDTMP, and the like.

The term thickening agent is the agent which is capable of building the viscosity of the solutions and comprise one or more of hydroxyethyl cellulose, hydroxypropylmethyl cellulose, methyl cellulose, xanthan gum, gellan gum, polyvinyl pyrrolidone, corbopols and the like.

Furthermore in yet another embodiment of the present invention, tonicity adjusting agents may be added and included without limitation such as glycerin, sorbitol, sodium hydroxide, sodium chloride, sodium borate, boric acid, potassium chloride, and mannitol, dextrose, propylene glycol and combinations thereof or any other suitable ophthalmically acceptable tonicity adjusting agents.

In one of the preferred embodiments, vehicles can also be used in the ophthalmic compositions of the present embodiments. These vehicles include, but are not limited to, methyl cellulose, hydroxypropyl methyl cellulose, poloxamers, carboxymethyl cellulose, hydroxyethyl cellulose, poly ethylene glycol, hyaluronic acid, polygalacturonic acid, xyloglucan, carbopol, polycarbophil, gellan gum physiological saline solution, water, purified water, and combinations thereof.

Additionally, suitable ophthalmic antioxidants if used may be selected from the group consisted of, but are not limited to sodium sulfite, potassium sulpfite, sodium metabisulfite, sodium thiosulfate, acetylcysteine, butylated hydroxyanisole, butylated hydroxytoluene, ascorbic acid and mixtures thereof.

In another embodiment, the surfactants if used may be selected from the group consisted of, but are not limited to sodium lauryl sulfate, docusate sodium, polyoxyalkyl ethers, polyoxylalkyl phenyl ethers, polyoxyl 40 hydrogenated castor oil (Cremophor RH 40), polyoxy hydrogenated castor oil, polyoxy sorbitan esters, sorbitan esters, polysorbates, polyoxyl 35 castor oil, sorbitan monolaureates, poloxamer and mixtures thereof.

The pH adjusting agents include hydrochloric acid, sodium hydroxide, phosphoric acid, acetic acid and the like. The buffering ingredients such as sodium chloride, sodium borate, sodium acetate, or gluconate buffers, and other conventional ingredients such as sorbitan monolaurate, triethanolamine, polyoxyethylene sorbitan monopalmitylate, dioctyl sodium sulfosuccinate, monothioglycerol, thiosorbitol, ethylenediamine tetra-acetic acid, and the like.

Additionally, suitable ophthalmic vehicles can be used as carrier media for the present purpose including conventional phosphate buffer vehicle systems, isotonic boric acid vehicles, isotonic sodium chloride vehicles, isotonic sodium borate vehicles and the like.

In a preferred embodiment, the solution would be an aqueous solution having a pH value within the range of from about 5.0 to about 7, preferably from about 5.5 to about 6.3 and osmolality in range of at least about 240 mOsmol/kg and/or less than or equal to about 350 mOsmol/kg.

Any pharmaceutically acceptable packaging material may be use, preferably packaging material that is suitable for containing ophthalmic pharmaceutical formulation, more preferably aqueous solution.

The aqueous solution is preferably sterile. An article comprising the aqueous solution filled in a container is preferably sterile, preferably at the time the container is filled. The aqueous solution is preferably filled into sterile multi-use or single-use containers, preferably single-use containers.

Several sterilizing grade membrane filters are available for aseptic filtration of water based pharmaceutical ophthalmic dosage forms such as cellulose acetate, nylon, polyether sulfone (PES), polypropylene (PP), polyvinyl difluoride (PVDF) and the like. The ophthalmic dosage form developed as a part of present invention has been tested for the sterility and is found to be sterile after multiple testing.

Pharmaceutically acceptable packaging materials include but are not limited to low density polyethylene ("LDPE"), high density polyethylene ("HDPE"), polypropylene, polystyrene, polycarbonate, polyesters (such as polyethylene terephthalate and polyethylene naphthalate), nylon, poly(vinyl chloride), poly(vinylidine chloride), poly(tetrafluoroethylene) and other materials known to those of ordinary skill in the art. Flexible bottles prepared from, or comprising, LDPE, HDPE or polypropylene are particularly preferred.

Preferred containers include bottles, preferably a dropper (e.g., a bottle or ampule suitable for dropwise application of the composition), more preferably, a single-use bottle or dropper. The containers are preferably sterilized, preferably prior to filling. Any suitable method can be used to sterilize the containers, and can be determined by the person of ordinary skill in the art. Some preferred methods include exposure to gamma irradiation and/or exposure to ethylene oxide gas.

The present invention provides a method of using the ophthalmic pharmaceutical formulation for treating ocular hypertension and glaucoma.

In a preferred embodiment, the present invention relates to the process of manufacturing ophthalmic pharmaceutical formulation for topical administration comprising dorzolamide and hydroxyl ethyl cellulose (HEC) in combination with timolol and/or ophthalmically acceptable carrier components wherein more specifically, the present invention is preferably devoid of BAC.

In further embodiment, the present inventors have embarked upon a simple technique, which eliminates the steam sterilization or autoclaving used in the prior.

In a preferred embodiment, the present invention provides a process of preparing preservative-free ophthalmic pharmaceutical formulation as disclosed in the above embodiments.

In operation, a first mixture of hydroxyethyl cellulose in water is heated to a temperature of about 94° C. to about 97° C. for sufficient time to produce a second mixture with a viscosity of about 100±10 centipoise. For example, the first mixture may be heated for about 7 to about 8 hours. In certain embodiments, the second mixture is heated to a temperature of about 95° C.

To the second mixture may be added active agents such as a carbonic anhydrase inhibitor and/or a beta adrenergic antagonist. Likewise, other additives such as a buffering agent and/or a tonicity adjusting agent may be added to the second mixture. The order of addition is not critical. For example, a buffering agent may be added prior to a tonicity adjusting agent or vice versa. Either buffering agents or tonicity adjusting agents may be added before or after the active agents. Alternatively, some or all of the additives and/or active agents may be added at or around the same time. Addition of a carbonic anhydrase inhibitor, a beta adrenergic antagonist, a buffering agent, and a tonicity adjusting agent to the second mixture produces a third mixture. In certain embodiments, the second mixture is cooled prior to further processing. For example, the second mixture may be cooled to about 25° C. to about 35° C. prior to processing the second mixture to the third mixture.

Adjustment of the pH of the third mixture produces a fourth mixture. In certain embodiments, the pH is adjusted to about 5.5 to about 6.3. In other embodiments, the pH is adjusted to about 5.6. The first mixture, second mixture, third mixture, and fourth mixture may all be prepared in the same tank.

The fourth mixture is sterilized by filtration through a sterile/aseptic filter to produce a fifth mixture that is sterile and preservative free. The filtration may be performed at any convenient temperature such as, for example, room temperature or about 45° C. Typically, the sterile filtration is through a filter with a pore size of about 0.2 microns.

The main embodiment of the present invention provides a method of manufacturing a sterile, preservative free ophthalmic formulation comprising:
  a. heating a first mixture of hydroxyethyl cellulose in water to a temperature of about 94° C. to about 97° C. for sufficient time to produce a second mixture with a viscosity of about 100±10 centipoise;
  b. dissolving a carbonic anhydrase inhibitor in the second mixture to produce a third mixture;
  c. adjusting the pH to between 5.5 to 6.0 to produce a fourth mixture; and
  d. sterilizing the fourth mixture by aseptic filtration to produce a fifth mixture which is sterile, preservative free ophthalmic formulation.

In another embodiment of the present invention, the method further comprises dissolving a beta adrenergic antagonist in the second mixture to produce the third mixture.

In another embodiment of the present invention, the method further comprises dissolving a buffering agent and a tonicity adjusting agent in the second mixture to produce the third mixture.

In another embodiment of the present invention, the fifth mixture comprises about 0.05% (w/v) to about 5% (w/v) of the carbonic anhydrase inhibitor.

In another embodiment of the present invention, the fifth mixture comprises about 0.01% (w/v) to about 1% (w/v) of the beta adrenergic antagonist.

In another embodiment of the present invention, the carbonic anhydrase inhibitor is dorzolamide hydrochloride.

In another embodiment of the present invention, the carbonic anhydrase inhibitor is dorzolamide hydrochloride and the beta adrenergic antagonist is timolol maleate.

In another embodiment of the present invention, the fifth mixture comprises about 2% dorzolamide hydrochloride (w/v) and about 0.5% timolol maleate (w/v).

In another embodiment of the present invention, the fifth mixture comprises about 1% dorzolamide hydrochloride (w/v) and about 0.5% timolol maleate (w/v).

In another embodiment of the present invention, the first mixture is heated at about 95° C. for sufficient time to produce the second mixture.

In another embodiment of the present invention, the first mixture is heated for about 7 to about 8 hours to produce the second mixture.

In another embodiment of the present invention, the buffering agent is sodium citrate dihydrate.

In another embodiment of the present invention, the tonicity adjusting agent is mannitol.

In another embodiment of the present invention, the pH is adjusted to about 5.6±0.1 with a sodium hydroxide solution.

In another embodiment of the present invention, the asceptic filtration comprises filtration through a sterilization filter with a pore size of about 0.2 microns.

In another embodiment of the present invention, the method further comprises adjusting the temperature of the fourth mixture to 45° C. prior to sterilization.

In another embodiment of the present invention, the method further comprises cooling the second mixture to about 25° C. to 35° C.

In another embodiment of the present invention, the first mixture, second mixture, third mixture, and fourth mixture are produced in the same tank.

In another embodiment of the present invention, the method further comprises adding one or more of a surfactant and/or an antioxidant.

Yet another embodiment of the present invention provides a stable ophthalmic formulation as prepared by process for manufacturing sterile, preservative free ophthalmic formulation.

In another embodiment of the present invention, the formulation is devoid of any preservative.

In another embodiment of the present invention, the ophthalmic formulation is packaged in a unit dose container.

Yet another embodiment of the present invention is to provide use of formulation for treating ocular hypertension and glaucoma, comprising applying once a day to an eye of a patient in need thereof.

In another embodiment of the present invention, the applying of formulation is done twice a day.

In another embodiment of the present invention, the applying of formulation is done at least once a day.

In another embodiment of the present invention, the formulation is stable when stored for 6 months at 40° C. at no more than 40% relative humidity.

In another embodiment of the present invention, the formulation which upon storage for 6 months at 40° C. at no more than 40% relative humidity, comprises less than 1.2 w/v % of impurity B {(4RS,6SR)-4-(Ethylamino)-6-methyl-5,6-dihydro-4H-thieno[2,3-b]thiopyran-2-sulfonamide 7,7-dioxide hydrochloride} of active ingredient dorzolamide.

Yet another embodiment of the present invention provides a method of treating ocular hypertension and glaucoma, comprising applying once a day to an eye of a patient in need thereof.

In another embodiment of the present invention, the applying of formulation is done twice a day.

In another embodiment of the present invention, the applying of formulation is done at least once a day.

Following sterilization, the sterile, preservative free ophthalmic solution may be packaged as described elsewhere herein.

EXAMPLES

The invention is illustrated by the following examples which are only meant to illustrate the invention and not act as limitation. All embodiments apparent to a process there in the art are deemed to fall within the scope of the present invention.

The term 'q.s.' wherever appears in the examples is an abbreviation for 'quantity sufficient' which is the amount of the excipient in such quantities that is just sufficient for its use in the composition of the present invention.

Formula 1:

| INGREDIENTS | QUANTITY mg/mL |
|---|---|
| Dorzolamide Hydrochloride USP/Ph. Eur. | 22.26 |
| Timolol Maleate USP | 6.83 |
| Hydroxy Ethyl cellulose USP NF | 4.5 |

-continued

Formula 1:

| INGREDIENTS | QUANTITY mg/mL |
|---|---|
| Mannitol USP/Ph. Eur./BP | 16.0 |
| Sodium Citrate (Dihydrate) USP/BP/Ph. Eur. (Biopharmaceutical Grade) | 2.94 |
| Sodium hydroxide USP NF/BP/Ph. Eur. (Biopharmaceutical Grade) | To adjust the pH |
| Water for injection USP/Ph. Eur./BP | q.s. to 1 mL |

FORMULA 2:

| INGREDIENTS | QUANTITY mg/mL |
|---|---|
| Dorzolamide Hydrochloride USP/Ph. Eur. | 11.13 |
| Timolol Maleate USP | 6.83 |
| Hydroxy Ethyl cellulose USP NF | 4.5 |
| Mannitol USP/Ph. Eur./BP | 16.0 |
| Sodium Citrate (Dihydrate) USP/BP/Ph. Eur. (Biopharmaceutical Grade) | 2.94 |
| Sodium hydroxide USP NF/BP/Ph. Eur. (Biopharmaceutical Grade) | To adjust the pH |
| Water for injection USP/Ph. Eur./BP | q.s. to 1 mL |

Manufacturing Process:
1. Weigh and check the weight of all the ingredients.
2. Part A—Preparation of hydroxy ethyl cellulose (HEC) solution—
   a. Take about 90% of batch size of Water for Injection (WFI) (65-85° C.) in a jacketed ss manufacturing tank.
   b. To this add slowly and disperse HEC under continuous stirring until it gets dissolve. Avoid lump formation during addition of HEC. Cool this solution up to 25° C. (between 20° C. to 30° C.) or till a clear and lump free solution obtained.
3. Part B—Heat Treatment of hydroxy ethyl cellulose (HEC) solution in tank—
   a. Increase the temperature of solution up to 95° C. and maintain the temperature between 94° C. to 97° C. for 7 to 8 hours. (Caution: Ensure the temperature of steam inside the jacket should be controlled by pressure valve with NMT 0.8 kg/cm2 pressure.)
   b. Cool this solution up to 30° C. (between 25° C. to 35° C.).
   c. Add and dissolve sodium citrate dihydrate in the above manufacturing tank under continuous stirring till it dissolves completely.
   d. Add and dissolve mannitol in the above manufacturing tank under continuous stirring till it dissolves completely.
   e. Add and dissolve dorzolamide hydrochloride in the above manufacturing tank under continuous stirring till it dissolves completely.
   f. Add and dissolve timolol maleate in the above manufacturing tank under continuous stirring till it dissolves completely.
   g. Adjust the pH of solution between 5.6±0.1 by 1N sodium hydroxide solution in increments. Stir the solution for 5 minutes after each addition.
   h. Make up the volume to 100% of batch size with WFI in above tank.
   i. Stir it for not less than 15 mins.
   j. Flush the headspace of manufacturing tank with nitrogen gas.

k. Increase the temperature to 45° C. (between 43° C.-47° C.).

4. Part C—Sterilization by filtration—
a. Filter the solution from manufacturing tank through a HDC II, 1.2 micron, 20", Code 7 PP Cartridge Filter followed by Supor EKV, 0.2 micron, 20", Code 7 PES Cartridge Filter into filtration tank. Discard one liter of product through T-Joint between Supor EKV, 0.2 micron, 20", Code 7 PES cartridge filter and filtration tank to saturate the filter. Mix it for NLT 15 min. (Caution: Ensure the pressure on manufacturing tank should be more than 3.5 kg/cm2 before starting the filtration and maintain the pressure between 3.5 to 4 kg/cm2 throughout the filtration.)
b. Start the online filtration from filtration tank through Supor EKV, 0.2 micron, 20", Code 7 PES Cartridge filter into a buffer tank at temperature between 25 to 30° C. and start the filling process.
c. Set the filling machines to provide targeted fill volume of 0.3 mL (range 0.26 to 0.34 mL).
d. Pack the product as per product packing instruction.

Stability Studies

A sterile, preservative free ophthalmic formulation of the present invention is prepared by the process described herein in the specification and is tested for stability against a control product (herein referred to as "COSOPT PF"). Six (6) months accelerated testing refers to storage at 40° C., at not more than 25% relative humidity (RH). Results for 6-months accelerated testing for both the control product (herein referred to as "COSOPT PF") and the present invention formulation are provided in Table 3.

An accelerated study comprises placing the composition/solution is filled in blow-fill-seal (BFS) LDPE vial, packing in aluminum foil, and maintaining at 40° C., at not more than 25% relative humidity (RH) in the dark.

As understood by those of skill in the art, when the drug comprises dorzolamide, the impurities preferably measured include Impurity D {(4S,6S)-4-Amino-6-methyl-5,6-dihydro-4H-thieno[2,3-b]thiopyran-2-sulfonamide7,7-dioxide hydrochloride} & {(4RS,6SR)-4-(Ethylamino)-6-methyl-5,6-dihydro-4H-thieno[2,3-b]thiopyran-2-sulfonamide 7,7-dioxide hydrochloride} and total impurities, as well as identification of the amount of the any independent unspecified impurity.

As understood by those of skill in the art, when the drug comprises timolol, the impurities preferably measured include Impurity G {4-Morpholino-1,2,5-thiadiazol-3-ol 1-oxide}; B {3-(tert-Butylamino)-2-(4-morpholino-1,2,5-thiadiazol-3-yloxy)propan-1-ol} and D {4-Morpholino-1,2,5-thiadiazol-3-ol}, and total impurities, as well as identification of the amount of the any independent unspecified impurity.

TABLE 3

Stability data of dorzolamide and timolol formulation (Formula 1) prepared by improved process, compared to control product (herein referred to as "COSOPT PF").

| Condition | | Initial | | 40° C./3M | | 40° C./6M | |
| --- | --- | --- | --- | --- | --- | --- | --- |
| Batch Description | Specification | Present Invention | Control product | Present Invention | Control product | Present Invention | Control product |
| Description | clear, colorless to nearly colorless, slightly viscous solution | Clear colorless solution | Clear colorless viscous solution | Clear colorless slightly viscous solution | Clear colorless viscous solution | Clear colorless slightly viscous solution | Clear colorless viscous solution |
| pH | approximately 5.65 (5.5-5.8) | 5.57 | 5.51 | 5.54 | 5.6 | 5.5 | 5.68 |
| Osmolality | 242-323 mOsM | 265 | 264 | 264 | 265 | 270 | 281 |
| Assay of Dorzolamide | 90.0-110.0% | 97.3 | 101.3 | 99.1 | 99.3 | 98.3 | 100 |
| Assay of Timolol | 90.0-110.0% | 98.4 | 98.8 | 98.9 | 101.3 | 99.9 | 101 |
| RS for Dorzolamide | Impurity D (NMT 0.5%) | 0.01 | 0.03 | 0.01 | 0.03 | 0.01 | 0.06 |
| | Impurity B (NMT 3.0%) | 0.05 | 0.2 | 0.47 | 1.04 | 0.94 | 2.25 |
| | Any independent unspecified impurity (NMT 0.5%) | BDL* | BDL | BDL | BDL | BDL | BDL |
| | Total impurity (NMT 3.0%) | 0.06 | 0.23 | 0.48 | 1.07 | 0.95 | 2.31 |

TABLE 3-continued

Stability data of dorzolamide and timolol formulation (Formula 1) prepared by improved process, compared to control product (herein referred to as "COSOPT PF").

| Condition | | Initial | | 40° C./3M | | 40° C./6M | |
|---|---|---|---|---|---|---|---|
| Batch Description | Specification | Present Invention | Control product | Present Invention | Control product | Present Invention | Control product |
| RS for Timolol | Impurity G (NMT 0.5%) | 0.01 | 0.01 | 0.01 | ND | BQL | ND |
| | Impurity B (NMT 0.5%) | 0.01 | 0.02 | 0.01 | 0.01 | 0.02 | 0.03 |
| | Impurity D (NMT 0.5%) | ND* | ND | ND | ND | ND | ND |
| | Any independent unspecified impurity (NMT 0.5%) | ND | BDL | BDL | BDL | BDL | BDL |
| | Total impurity (NMT 2.0%) | 0.02 | 0.03 | 0.02 | 0.01 | 0.02 | 0.03 |

*Below detection limit.
**None detected.

Results and Observations

The controlled product ("herein referred to as "COSOPT PF") is evaluated for active ingredients content and related substances at initial; at 3 months and at 6 months for accelerated stability at 40° C., at not more than 25% relative humidity (RH) in the dark. Results are shown in Table 3.

The present invention formulation is evaluated for active ingredients content and related substances at initial; at 3 months and at 6 months for accelerated stability at 40° C., at not more than 25% relative humidity (RH) in the dark. Results are shown in Table 3.

The results of the conducted comparative accelerated stability studies between control product and present invention formulation is compared and the formulation(s) prepared by the process of the present invention are unexpectedly more stable than that of control product and this is depicted by the impurities profiles of "Impurity B" for the active ingredient dorzoalmide. The "Impurity B" of active ingredient dorzoalmide for the present invention formulation is significantly lower (0.94% at 6 months) than that of control product (2.25% at months) i.e. in a neutral pH range. Hence, the product manufactured by this improved process of the present invention is more stable than the control product, COSOPT PF.

UTILITY OF THE PRESENT INVENTION

The present inventors provides a simpler, cost effective process for manufacturing sterile, preservative free ophthalmic formulation in a single tank, without the use of additional tanks that can be sterile filtered. The prepared formulation is devoid of benzalkonium chloride or any other preservatives. The prepared formulation is used in treating ocular hypertension and glaucoma.

The invention claimed is:

1. A method of manufacturing a sterile, preservative free ophthalmic formulation solution without steam sterilization or autoclaving comprising:
   a) heating a first mixture comprising a first solution that consists essentially of hydroxyethyl cellulose dissolved in water and is devoid of any preservative to a temperature of about 94° C. to about 97° C. for a sufficient time to produce a second mixture comprising a second solution having viscosity of about 100±10 centipoise and devoid of any preservative;
   b) dissolving a carbonic anhydrase inhibitor in the second mixture to produce a third mixture comprising a third solution that is devoid of any preservative, wherein the carbonic anhydrase inhibitor comprises dorzolainide, or a salt thereof;
   c) adjusting pH of the third mixture to between 5.5 to 6.0 to produce a fourth mixture comprising a fourth solution that is devoid of any preservative and heating the fourth mixture to between 43° C. to 47° C.; and
   d) sterilizing the fourth mixture by aseptic filtration which comprises filtration through a sterilization filter having a pore size of about 0.2 microns to produce a fifth mixture which is a sterile, preservative free ophthalmic formulation solution that is devoid of any preservative and that is produced without steam sterilization or autoclaving.

2. The method of claim 1 further comprising dissolving a beta adrenergic antagonist in the second mixture to produce the third mixture.

3. The method of claim 1 further comprising dissolving a buffering agent and a tonicity adjusting agent in the second mixture to produce the third mixture.

4. The method of claim 1 wherein the fifth mixture comprises about 0.05% (w/v) to about 5% (w/v) of the carbonic anhydrase inhibitor.

5. The method of claim 2 wherein the fifth mixture comprises about 0.01% (w/v) to about 1% (w/v) of the beta adrenergic antagonist.

6. The method of claim 1 wherein the carbonic anhydrase inhibitor consists of dorzolamide hydrochloride.

7. The method of claim 2 wherein the beta adrenergic antagonist is timolol maleate.

8. The method of claim 7 wherein the fifth mixture comprises about 2% dorzolamide hydrochloride (w/v) and about 0.5% timolol maleate (w/v).

9. The method of claim 7 wherein the fifth mixture comprises about 1% dorzolamide hydrochloride (w/v) and about 0.5% timolol maleate (w/v).

10. The method of claim 1 wherein the first mixture is heated at about 95° C. for sufficient time to produce the second mixture.

11. The method of claim 1 wherein the first mixture is heated for about 7 to about 8 hours to produce the second mixture.

12. The method of claim 3 wherein the buffering agent is sodium citrate dihydrate.

13. The method of claim 3 wherein the tonicity adjusting agent is mannitol.

14. The method of claim 1 wherein the pH of the third mixture is adjusted to about 5.6 ±0.1 with a sodium hydroxide solution to produce the fourth mixture.

15. The method of claim 1, which comprises heating the fourth mixture to 45° C. prior to sterilization.

16. The method of claim 1 further comprising cooling the second mixture to about 25° C. to 35° C. prior to dissolving the carbonic anhydrase inhibitor.

17. The method of claim 1 wherein the first mixture, second mixture, third mixture, and fourth mixture are produced in a single tank.

18. The method of claim 1 further comprising adding one or more of a surfactant and an antioxidant to the ophthalmic formulation.

* * * * *